United States Patent [19]
Jörnéus et al.

[11] Patent Number: 5,259,759
[45] Date of Patent: Nov. 9, 1993

[54] TEMPORARY CYLINDER

[75] Inventors: Lars Jörnéus, Frillesas; Stefan Edgren, Kullavik; Thomas Svensson, Göteborg, all of Sweden

[73] Assignee: Nobelpharma AB, Göteborg, Sweden

[21] Appl. No.: 858,518

[22] Filed: Mar. 27, 1992

[30] Foreign Application Priority Data

Mar. 27, 1991 [SE] Sweden ............... 9100913-4

[51] Int. Cl.⁵ .................................................. A61C 8/00
[52] U.S. Cl. ........................................................ 433/173
[58] Field of Search ................. 433/173, 174, 175, 176

[56] References Cited

U.S. PATENT DOCUMENTS

| | | | |
|---|---|---|---|
| 4,780,080 | 10/1988 | Haris | 433/173 |
| 4,850,873 | 7/1989 | Lazzara | 433/220 |
| 4,906,191 | 3/1990 | Soderberg | 433/173 |
| 5,006,069 | 4/1991 | Lazzara et al. | 433/173 |
| 5,073,111 | 12/1991 | Daftary | 433/173 |
| 5,078,606 | 1/1992 | Soderberg | 433/173 |
| 5,135,395 | 8/1992 | Marlin | 433/174 |

FOREIGN PATENT DOCUMENTS

| | | |
|---|---|---|
| 0313222 | 4/1989 | European Pat. Off. |
| 2824214 | 12/1979 | Fed. Rep. of Germany |
| 3711884 | 10/1988 | Fed. Rep. of Germany |
| 8905688 | 11/1989 | Fed. Rep. of Germany |
| 2623709 | 6/1989 | France |

Primary Examiner—Cary E. O'Connor
Attorney, Agent, or Firm—Pollock Vande Sande & Priddy

[57] ABSTRACT

The invention relates to a cylinder 1 designed to be inserted in a temporary, implant-supported dental bridge/dental prosthesis,, a so-called temporary cylinder, and which comprises an upper part 2 which is surrounded by the dental bridge/dental prosthesis and a base section 4 for connection to the spacer element 6 of the implant. The cylinder is made of a polymer material and the upper part 2 has a conical outer contour.

8 Claims, 1 Drawing Sheet

FIG. 1
FIG. 2
FIG. 3
FIG. 4
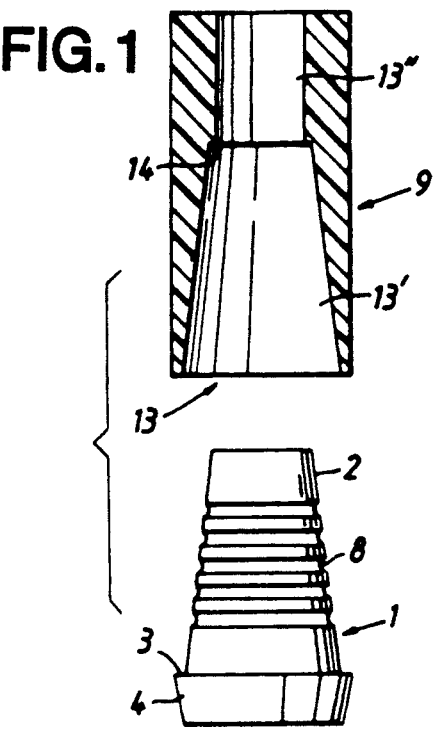
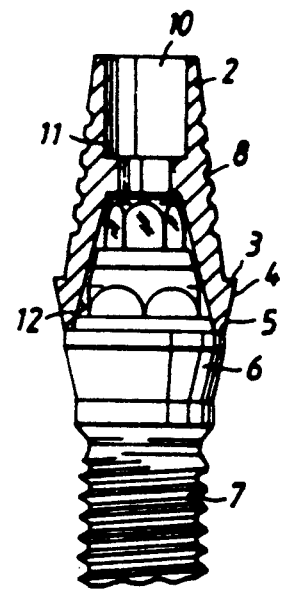
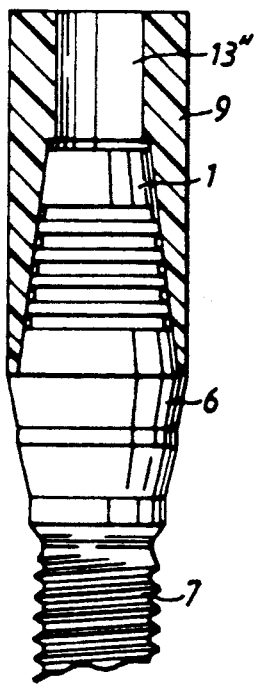
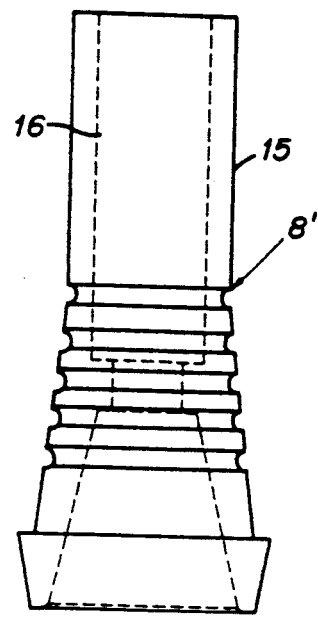

TEMPORARY CYLINDER

FIELD OF THE INVENTION

The present invention relates to a cylinder of the type which is designed to be inserted in a temporary, implant-supported dental bridge/dental prosthesis, a so-called temporary cylinder.

BACKGROUND OF THE INVENTION

It is already known to permanently anchor a dental prosthesis in the jaw with the aid of titanium screws implanted in the jawbone. The screws are anchored in holes in the bone in au lee that the upper part of the screw is located leveled with or immediately below the top surface of the jawbone. The screw is then covered over with a flap of raucous membrane and is left unloaded for a rest period of 3 to 6 months so that the bone can grow securely to and form a unit with the implanted screw. After the rest period the screw is exposed and a spacer element, preferably also of titanium, is arranged on the screw, after which a dental prosthesis is anchored on the spacer element. The dental prosthesis must in this case be adapted accurately to the actual appearance of the jaw with the implanted titanium elements.

After the spacing operation has been carried out, the treated patient wants to have the dental prosthesis ready as soon as possible. At present it takes a relatively long time for an aesthetically optimal dental prosthesis to be produced. This is partly because the skilled work of dental technicians and dentists takes a certain time to carry out , but primarily because the raucous membrane/gum around the spacers in most cases recedes, and this means that the spacers may become visible. In most cases this is undesirable.

Many dentists therefore want to produce a temporary dental prosthesis/dental bridge which is relatively simple in its design and for which the aesthetically optimal solution is not sought. In terms of the work involved, such a dental prosthesis is simpler and faster to produce, which means that the patient is given it very soon after the spacing operation. When the raucous membrane has receded after a month or a few months, it is possible to begin work on the final dental bridge.

Hitherto, these temporary solutions have involved the use of gold cylinders which are intended to be cast into the finished dental bridge. However, these cylinders are relatively expensive, primarily on account of high material costs, since they are made of an alloy consisting of gold and platinum.

Temporary bridges can be divided into two types: those which are made entirely of acrylic resin and those which have a cast metal skeleton in order to increase their strength.

There are, in addition, on the market metal cylinders made from less expensive material which are intended for temporary use. These cylinders can be made of, for example, aluminium or stainless steel. However, these materials are not entirely satisfactory; aluminium on account of toxicity, and stainless steel on account of the tendency to corrosion together with titanium. In addition, these cylinders also require a mechanical working which, if it is to be carried out with precision, is relatively costly.

SUMMARY OF THE PRESENT INVENTION

The purpose of this invention is to provide a cylinder for temporary use which solves the above problems. A cylinder for use in a temporary, implant-supported dental bridge/dental prosthesis, according to the present invention comprises a cylinder member made of a polymer material and including an upper part which is surrounded by the dental bridge/dental prosthesis. The upper part has a conical outer contour provided with means for increased retention against the surrounding dental bridge/dental prosthesis. The conical upper part also includes a cylindrical top portion. The cylinder also includes a base section for connection to a spacer element of the implant.

BRIEF DESCRIPTION OF THE DRAWINGS

Two embodiments of the invention are shown diagrammatically in the attached drawing, in which:

FIG. 1 shows the cylinder and a cooperating outer sleeve according to the present invention.

FIG. 2 shows the cylinder in a cutaway view applied on a conical spacer;

FIG. 3 shows both cylinder and outer sleeve applied on a conical spacer; and

FIG. 4 shows an alternative embodiment of the cylinder.

DETAILED DESCRIPTION OF THE PREFERRED EMBODIMENT

The cylinder of the present invention is made of a high-strength, non-toxic structural polymer, for example polyetheretherketone PEEK. It is designed in such a way that greater flexibility is obtained as regards the manner of application. Previously known temporary cylinders have an outer contour of essentially cylindrical shape. This means that they must be joined together with the dental bridge outside the patient's mouth. In most cases this is carried out in a dental laboratory.

In contrast to these previously known temporary cylinders, the cylinder 1 according to the invention has an upper part 2 of conical outer shape, which means that the joining together can also be performed in the patient's mouth, which can be of great advantage if, for example, it is desired to convert the patient's old dental prosthesis to an implant-supported temporary bridge directly upon connection of the spacer. In this case, the conical seats are filled up in this dental prosthesis, and the dental bridge is cemented, or alternatively fitted with so-called cold-setting acrylate, on the temporary cylinders screwed into the patient.

The conical upper part 2 merges at the bottom, via an annular shoulder 3, into a conical, downwardly tapering base section 4 which is intended to bear against a shoulder 5 of a conical spacer 6, see FIG. 2, for example a conical spacer according to SE 8903038-1, arranged on a fixture 7. In order to increase the retention against the surrounding dental bridge, the outer contour of the cylinder is provided with grooves 8.

The cylinder 1 is sleeve-shaped and has a through-hole (screw channel) which consists of an upper cylindrical recess 10, a seat 11 for the screw (not shown in the figure) which holds the cylinder securely against the conical spacer, and a lower conical opening 12 inside which the upper conical section of the spacer is accommodated.

With the temporary cylinder 1, an outer sleeve 9 made of a material which can burn out, for example acrylic resin, can be used. An outer sleeve of this type can give improved precision on direct cementing in accordance with the method which has been described above. However, the most important function is to form a mold when it is desired to produce the temporary bridge with a metal skeleton for increased strength. The finished dental bridge can then be joined together with the temporary cylinders in the dental laboratory with screw channels retained, or cemented/secured with resin in the patient's mouth on the temporary cylinders previously screwed in.

The outer sleeve 9 is dimensioned in such a way that it fits the temporary cylinder with a suitable play. The procedure described above, in which the temporary cylinders are secured in the final stage of the process, thus affords a very important advantage as compared with the conventionally used methods. The errors, such as the inadequate casting accuracy and the like, which always arise and which can lead to considerable stresses being built into the construction, can be eliminated almost entirely by means of this predetermined play between the temporary cylinder and the outer sleeve. The errors are resolved entirely by virtue of the fact that the gap can have a varying thickness. Since in this way an extremely good precision is obtained, the load on the dental implants is reduced. In addition, the intrinsic resiliency properties of the resin contribute to reducing the transient loads which can occur during mastication.

The outer sleeve 9 also has a continuous channel 13 which consists of a lower, conical recess 13' inside which the conical upper part of the cylinder is accommodated, and a narrower, upper cylindrical channel 13''. An inner shoulder 14 bears against the upper end surface of the cylinder, and the base section of the outer sleeve bears against the annular shoulder of the cylinder.

Instead of using a separate outer sleeve 9 the conical upper part of the cylinder can be made with a cylindrical top portion 15 as illustrated in FIG. 4. The cylindrical top portion 15 has substantially the same length as the conical upper part of the cylinder. Such embodiment then provides an increased surface between the cylinder and the temporary bridge, which means increased stability between the cylinder and the acrylic temporary bridge, and also an elongated channel 16 for the bridge securing screw. If this type of cylinder is used with a separate outer sleeve 9, however, then the cylindrical top portion 15 is shortened, preferably the cylinder is cut at the top groove 8'. The grooves then serve both as retention means and cutting mark for shortening the cylinder.

We claim:

1. A cylinder for use in a temporary, implant-supported dental bridge/dental prosthesis, said cylinder comprising:
   a cylinder member made of a polymer material and including an upper part which is surrounded by the dental bridge/dental prosthesis, said upper part having a conical outer contour provided with retaining means for increased retention against the surrounding dental bridge/dental prosthesis, said conical upper part also including a cylindrical top portion, and a base section for connection of the cylinder to a spacer element of the implant.

2. A cylinder according to claim 1 wherein said retaining means includes a plurality of grooves.

3. A cylinder according to claim 2 wherein an upper groove of said plurality of grooves defines a cutting mark for shortening the cylinder member.

4. A cylinder according to claim 1 wherein the conical upper part merges into said base section through an annular shoulder, and wherein said base section also has a conical outer contour which, is tapered downwards in order to fit the outer contour of the spacer element.

5. A cylinder according to claim 1 wherein said cylindrical top portion has substantially the same length as the conical upper part of the cylinder member.

6. A cylinder assembly for use in a temporary, implant-supported dental bridge/dental prosthesis, said cylinder comprising:
   a cylinder member made of a polymer material and including an upper part to be surrounded by the dental bridge/dental prosthesis, and having a conical outer contour, and an outer sleeve insertable on said cylinder and designed to fit with a suitable play to allow accommodation of any dimensional change during the casting process or during polymerization of the bridge framework.

7. A cylinder assembly according to claim 6 wherein said outer sleeve is made of a burn-out resin.

8. A cylinder assembly according to claim 6 wherein said outer sleeve includes a base section which bears against an annular shoulder of said cylinder member.

* * * * *